(12) United States Patent
Florence et al.

(10) Patent No.: US 9,028,892 B2
(45) Date of Patent: *May 12, 2015

(54) TOPICAL SKIN CARE FORMULATIONS COMPRISING JABOTICABA AND CASHEW FRUIT PULPS AND EXTRACTS THEREOF

(71) Applicant: Mary Kay Inc., Dallas, TX (US)

(72) Inventors: Tiffany Florence, Dallas, TX (US); David Gan, Southlake, TX (US); Michelle Hines, Hickory Creek, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/295,023

(22) Filed: Jun. 3, 2014

(65) Prior Publication Data

US 2014/0356467 A1    Dec. 4, 2014

Related U.S. Application Data

(63) Continuation of application No. 13/821,913, filed as application No. PCT/US2011/049184 on Aug. 25, 2011, now Pat. No. 8,747,927.

(60) Provisional application No. 61/381,677, filed on Sep. 10, 2010.

(51) Int. Cl.
| A61K 36/00 | (2006.01) |
| A61K 8/97 | (2006.01) |
| A61Q 19/00 | (2006.01) |
| A61Q 19/08 | (2006.01) |
| A61K 47/34 | (2006.01) |

(52) U.S. Cl.
CPC ............... *A61K 8/97* (2013.01); *A61Q 19/007* (2013.01); *A61Q 19/08* (2013.01); *A61K 47/34* (2013.01); *A61K 2800/40* (2013.01)

(58) Field of Classification Search
None
See application file for complete search history.

(56) References Cited

U.S. PATENT DOCUMENTS

| 6,156,297 A | 12/2000 | Maurin et al. |
| 6,818,234 B1 * | 11/2004 | Nair et al. ............ 424/777 |
| 7,014,844 B2 | 3/2006 | Mahalingam et al. |
| 8,747,927 B2 * | 6/2014 | Florence et al. ............ 424/777 |
| 2005/0249758 A1 | 11/2005 | Di Puccio Pagano |
| 2009/0068255 A1 * | 3/2009 | Yu et al. ............ 424/450 |
| 2009/0117211 A1 * | 5/2009 | Schneider et al. ............ 424/747 |
| 2010/0233128 A1 | 9/2010 | Panasenko |

FOREIGN PATENT DOCUMENTS

| EP | 1 992 322 | 11/2008 |
| JP | 2001122731 | 5/2001 |
| WO | WO 2008/006582 | 1/2008 |
| WO | WO 2008/006589 | 1/2008 |

OTHER PUBLICATIONS

English translation of Ohara ( JP 2001-122731) 2001.*
de Assis et al., "Antioxidant activity, ascorbic acid and total phenol of exotic fruits occurring in Brazil," *International Journal of Food Sciences and Nutrition*, 60(5):439-448, 2009.
Favaro, "Extraction, stability and qualification of anthocyanins of Brazilian typical fruits for industrial application as colorants," *Universidade Estadual de Campinas Instituo de Quimica*, 2007.
International Preliminary Report on Patentability issued in PCT Application No. PCT/US2011/049184, mailed Mar. 28, 2013.
International Search Report and Written Opinion issued in PCT Application No. PCT/US2011/049184, mailed Mar. 5, 2013.
Okonkwo et al., "Sub-chronic Hepatotoxicity of *Anacardium occidentale* (Anacardiaceae) Inner Stem Bark Extract in Rats," *Indian Journal of Pharmaceutical Sciences*, 73(3):353-357, 2010.

* cited by examiner

*Primary Examiner* — Susan Hoffman
(74) *Attorney, Agent, or Firm* — Norton Rose Fulbright US LLP

(57) ABSTRACT

Disclosed are compositions and corresponding methods of their use that include jaboticaba fruit pulp and/or cashew fruit pulp or extracts thereof.

10 Claims, No Drawings

TOPICAL SKIN CARE FORMULATIONS COMPRISING JABOTICABA AND CASHEW FRUIT PULPS AND EXTRACTS THEREOF

CROSS REFERENCE TO RELATED APPLICATIONS

This application is a continuation of U.S. application Ser. No. 13/821,913 filed Apr. 24, 2013, now U.S. Pat. No. 8,747,927, which is a national phase application under 35 U.S.C. §371 of International Application No. PCT/US2011/049184 filed Aug. 25, 2011, which claims the benefit of U.S. Provisional Application No. 61/381,677, filed Sep. 10, 2010. The contents of the referenced applications are incorporated by reference.

BACKGROUND OF THE INVENTION

A. Field of the Invention

The present invention relates generally to compositions that include jaboticaba and/or cashew fruit pulp or extracts thereof. The compositions can be formulated as topical skin compositions, edible compositions, injectable compositions, oral compositions, hair care compositions, etc.

B. Description of Related Art

Ageing, chronic exposure to adverse environmental factors, malnutrition, fatigue, etc., can change the visual appearance, physical properties, or physiological functions of skin in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious, but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

Previous attempts to improve the visual appearance of skin with known skin active-ingredients have been shown to have various drawbacks such as causing erythema (e.g., reddening of the skin).

SUMMARY OF THE INVENTION

The present invention provides an effective alternative to existing skin treatment compositions. The compositions of the present invention can have a dual effect in both treating skin conditions while also reducing or preventing erythema that can be caused by the very composition being applied to skin. In this sense, the compositions of the present invention can treat skin without the various drawbacks seen in prior art compositions.

In one non-limiting aspect of the invention, there is disclosed a topical skin care composition comprising an effective amount of jaboticaba fruit pulp and/or cashew fruit pulp or extracts thereof to increase hyaluronic acid synthesis and inhibit COX-1 and TNF-α synthesis in skin during use; and a dermatologically acceptable vehicle. The dermatologically acceptable carrier can include 25% to 35% by weight of water, at least 35% by weight of a silicone phase comprising cyclopentasiloxane, polysilicone-11, PEG-10 dimethicone, and dimethicone, and 3% to 7% by weight of silica. The dermatologically acceptable carrier can further include 3% to 5% by weight of glycerin, 1 to 3% by weight of pentylene glycol, and 1% to 3% by weight of caprylic/capric triglyceride. In another aspect, the dermatologically acceptable vehicle can include 60% to 70% by weight of water, 5% to 10% by weight of alcohol, 5% to 10% by weight of dipropylene glycol, 1% to 5% by weight of methyl gluceth-20, 1% to 5% by weight of biosaccharide gum, 1% to 5% by weight of glyceryin and 1% to 5% by weight of dimethicone/vinyl dimethicone crosspolymer. One of the unique aspects of these two types of dermatologically acceptable carriers is that they surprising have excellent tactile properties/are cosmetically elegant, are safe to use on skin, and provide an environment which allows for the jaboticaba and/or cashew fruit extracts to remain stable and effective while also allowing for efficient distribution of said extracts to skin once the composition is topically applied to said skin. It is for this reason (efficient distribution) that minimal amounts of these extracts are needed in the composition to bring about the desired results (e.g., as little as 0.01% by weight of each extract can be used, with a more desirable range being between 0.01% to 1%, while a broader range can also be used if desired such as 0.01% to 20%), 0.1% to 10% by weight, or 0.5% to 5% by weight of jaboticaba fruit pulp and/or cashew fruit pulp. The topical skin care composition can be a lotion, cream, serum, or emulsion. The jaboticaba fruit pulp and/or cashew fruit pulp can be powdered form when added to the composition. The composition in certain aspects does not include any other parts of the jaboticaba and/or cashew plants (e.g., nut, bark, leaf, etc.) or any other extracts thereof and does not include jaboticaba oil and/or cashew oil. The composition in certain aspects does not include hyaluronic acid, carboxymethyl cysteamine compound, and/or a rosehip extract. In addition the compositions can be used in a method for treating a skin condition comprising topically applying to skin in need thereof said composition, wherein said composition increases hyaluronic acid synthesis and inhibits COX-1 and TNF-α synthesis in the skin. The composition can be applied to a fine line or wrinkle or erythemic skin.

In addition to the above paragraph, there are also contemplated a wide range of various uses. For instance, in one non-limiting aspect of the present invention, there is disclosed a method of treating a skin condition comprising topically applying to skin in need thereof a composition comprising jaboticaba fruit pulp and/or cashew fruit pulp, or extracts thereof (e.g., aqueous extracts of the pulp, alcohol extracts of the pulp, oil extracts of the pulp, aqueous/alcohol extracts of the pulp, glycolic extracts of the pulp, etc.), wherein the composition increases hyaluronic acid synthesis and inhibits COX-1 and TNF-α, synthesis in the skin. The composition can be applied to a wide variety of skin conditions that can be treated or prevented by increasing hyaluronic acid synthesis, inhibiting or reducing COX-1 activity, and/or inhibiting or reducing TNF-α activity in the skin. In one aspect, the composition can be applied to a fine line or wrinkle, erythemic skin, or inflamed skin. The composition can also be used to treat or prevent other skin diseases and conditions that are disclosed throughout this specification. In particular aspects, the composition can include 0.0001% to 20% by weight of jaboticaba fruit pulp and/or cashew fruit pulp, or extracts thereof. In other instances, the compositions can include 0.001, 0.01, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 6, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%, or more (or any range or integer therein) of jaboticaba fruit pulp and/or cashew fruit pulp, or extracts thereof. The composition can be formulated as a lotion, cream, gel, serum, emulsion, anhydrous product, or in powdered form. In particular embodiments, the jaboticaba fruit pulp and/r cashew fruit pulp or extracts thereof are dried or lyophilized. In certain instances, the composition does not include hyaluronic acid, does not include any other plant materials or extracts thereof, does not include any other parts of the jaboticaba and cashew plants or any other extracts of the jaboticaba and cashew, does not include a carboxymethyl cysteamine compound, does not include a rosehip extract, does not include jaboticaba oil, does not include cashew oil, and/or does not include cashew nut or extracts thereof. The composition can further comprise a moisturizing agent, a silicone containing compound, a UV absorbing agent, a structuring agent, a viscosity modifying agent, an emulsifier or surfactant, a vitamin, a mineral, and/or any other ingredients known to those having skill in the art and disclosed in this specification. Non-limiting examples of skin conditions include dry skin, flaky skin, chapped skin, pruritus, spider veins, lentigo, age spots, senile purpura, keratosis, melasma, blotches, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, sun burns, burned skin, open wounds, skin-inflammatory skin conditions, etc. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein.

In another embodiment there is disclosed a topical skin care composition comprising: an effective amount of jaboticaba fruit pulp and/or cashew fruit pulp or extracts thereof (e.g., aqueous extracts of the pulp, alcohol extracts of the pulp, oil extracts of the pulp, aqueous/alcohol extracts of the pulp, glycolic extracts of the pulp, etc.) to increase hyaluronic acid synthesis and inhibit COX-1 and TNF-α synthesis in skin during use; and a dermatologically acceptable vehicle. The topical skin care composition can include 0.0001% to 20% by weight of jaboticaba fruit pulp and/or 0.0001% to 20% by weight of cashew fruit pulp or extracts thereof. In other instances, the compositions can include 0.001, 0.01, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 6, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%, or more (or any range or integer therein) of jaboticaba fruit pulp and/or cashew fruit pulp, or extracts thereof. The composition can be formulated as a lotion, cream, gel, serum, emulsion, anhydrous product, or in powdered form. In particular embodiments, the jaboticaba fruit pulp and/r cashew fruit pulp or extracts thereof are dried or lyophilized. In certain instances, the composition does not include hyaluronic acid, does not include any other plant materials or extracts thereof, does not include any other parts of the jaboticaba and cashew plants or any other extracts of the jaboticaba and cashew, does not include a carboxymethyl cysteamine compound, does not include a rosehip extract, does not include jaboticaba oil, does not include cashew oil, and/or does not include cashew nut or extracts thereof. The composition can further comprise a moisturizing agent, a silicone containing compound, a UV absorbing agent, a structuring agent, a viscosity modifying agent, an emulsifier or surfactant, a vitamin, a mineral, and/or any other ingredients known to those having skill in the art and disclosed in this specification. In a particular instance, the composition can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 6, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% by weight of water.

In one particular aspect there is disclosed a method of treating or preventing a fine line or wrinkle comprising topically applying to skin in need thereof a composition comprising jaboticaba fruit pulp and/or cashew fruit pulp or extracts thereof (e.g., aqueous extracts of the pulp, alcohol extracts of the pulp, oil extracts of the pulp, aqueous/alcohol extracts of the pulp, glycolic extracts of the pulp, etc.), wherein topical application of said composition to a fine line or wrinkle treats said fine line or wrinkle.

In yet another embodiment there is disclosed a method of treating or preventing erythemic skin or symptoms associated with erythemic skin (e.g., red skin, flushed skin, etc.) comprising topically applying to skin in need thereof a composition comprising jaboticaba fruit pulp and/or cashew fruit pulp or extracts thereof (e.g., aqueous extracts of the pulp, alcohol extracts of the pulp, oil extracts of the pulp, aqueous/alcohol extracts of the pulp, glycolic extracts of the pulp, etc.), wherein topical application of said composition to erythemic skin treats said erythemic skin. Erythema can be caused by skin irritation, an inflammatory response, skin sunburn, electrical treatments of skin, skin burns, contact allergies, systemic allergies, skin toxicity, exercise, insect stings, bacterial infection, viral infection, fungal infection, protozoa infection, massage, windburn, and other factors that can cause reddening or flushing of the skin etc. The compositions disclosed above and throughout this specification can be used. The compositions can also be used to reducing pain associated with erythema, sensitive skin, or inflamed skin, comprising topically applying to erythemic, sensitive, or inflamed skin a composition comprising jaboticaba fruit pulp and/or cashew fruit pulp or extracts thereof.

Also disclosed is a method of tightening or toning skin comprising topically applying to skin in need thereof a composition comprising jaboticaba fruit pulp and/or cashew fruit pulp or extracts thereof (e.g., aqueous extracts of the pulp, alcohol extracts of the pulp, oil extracts of the pulp, aqueous/alcohol extracts of the pulp, glycolic extracts of the pulp, etc.), wherein topical application of said composition to skin tightens or tones said skin. The compositions disclosed above and throughout this specification can be used.

In even a further embodiment there is disclosed an ingestible composition comprising jaboticaba fruit pulp and/or cashew fruit pulp or extracts (e.g., aqueous extracts of the pulp, alcohol extracts of the pulp, oil extracts of the pulp, aqueous/alcohol extracts of the pulp, glycolic extracts of the pulp, etc.) thereof and an ingestible acceptable vehicle. In certain aspects, the ingestible composition can be a food-based product, a pill, a gel capsule, a powder, or a neutraceutical product.

An additional embodiment includes an injectible solution comprising jaboticaba fruit pulp and/or cashew fruit pulp or extracts thereof (e.g., aqueous extracts of the pulp, alcohol extracts of the pulp, oil extracts of the pulp, aqueous/alcohol extracts of the pulp, glycolic extracts of the pulp, etc.) and an injectibly acceptable solution. Injectibly acceptable solution includes a solution that can be safely injected into a human or animal.

One embodiment concerns a method of treating or preventing a disease comprising administering to a person in need thereof jaboticaba fruit pulp and/or cashew fruit pulp or extracts thereof (e.g., aqueous extracts of the pulp, alcohol extracts of the pulp, oil extracts of the pulp, aqueous/alcohol extracts of the pulp, glycolic extracts of the pulp, etc.), wherein the disease is treated or prevented. Non-limiting examples of diseases include AIDS, an autoimmune disease (e.g., rheumatoid arthritis, multiple sclerosis, diabetes—insulin-dependent and non-independent, systemic lupus erythematosus, or Graves disease), a cancer (e.g., malignant, benign, metastatic, or precancer), a cardiovascular disease (e.g., heart disease, or coronary artery disease, stroke—ischemic and hemorrhagic, or rheumatic heart disease), diseases of the nervous system, an infection by a pathogenic microorganism (e.g., Athlete's Foot, Chickenpox, Common cold, Diarrheal diseases, Flu, Genital herpes, Malaria, Meningitis, Pneumonia, Sinusitis, Skin diseases, Strep throat, Tuberculosis, Urinary tract infections, Vaginal infections, or Viral hepatitis), inflammation (e.g., allergy, or asthma), a prion disease (e.g., CJD, kuru, GSS, or FFI), or obesity.

A further embodiment includes a method of treating or preventing hair loss comprising administering to a patient in need thereof a composition comprising jaboticaba fruit pulp and/or cashew fruit pulp or extracts thereof (e.g., aqueous extracts of the pulp, alcohol extracts of the pulp, oil extracts of the pulp, aqueous/alcohol extracts of the pulp, glycolic extracts of the pulp, etc.). The composition can included a pharmaceutically (whether topical, oral, injectible, etc.) or dermatologically acceptable vehicle, wherein administering to the patient in need thereof prevents or treats hair loss. Preventing or treating hair loss can include stimulating hair growth on the scalp, in eyebrows, in eyelashes, or on other regions of the body where hair growth is desired. The composition can take the form of an edible pill or gel cap or liquid or powder or foam or spray or aerosolized. The composition can be topically applied, ingested, injected, etc.

In addition there is disclosed a composition comprising jaboticaba fruit pulp and/or cashew fruit pulp or extracts thereof (e.g., aqueous extracts of the pulp, alcohol extracts of the pulp, oil extracts of the pulp, aqueous/alcohol extracts of the pulp, glycolic extracts of the pulp, etc.). The compositions can be formulated into topical skin or hair care compositions. The compositions can be cosmetic compositions. The compositions can be edible compositions. The compositions can be injectible compositions. The compositions can take the form of a pill, gel capsule, spray, foam, or be aerosolized. The compositions can be formulated as emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (e.g., aqueous or hydro-alcoholic solutions), anhydrous bases (e.g., lipstick or a powder), gels, ointments, milks, pastes, aerosols, solid forms, eye jellies, etc. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.). The compositions of the present invention can include any desired amount of jaboticaba or cashew extract or both. The amount of the extracts can individually or combined be from 0.001, 0.01, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 6, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%, or more (or any range or integer therein), by weight or volume of the extract or combination of extracts. The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride caprylic capric triglyceride). The compositions can also include preservatives. Non-limiting examples of preservatives include methylparaben, propylparaben, or a mixture of methylparaben and propylparaben. Compositions of the present invention can have UVA and UVB absorption properties. The compositions can have an sun protection factor (SPE) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

In one aspect of the present invention, there is disclosed a topical skin care composition that includes jaboticaba fruit pulp and/or cashew fruit pulp or extracts thereof (e.g., aqueous extracts of the pulp, alcohol extracts of the pulp, oil extracts of the pulp, aqueous/alcohol extracts of the pulp, glycolic extracts of the pulp, etc.) in combination with any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Also disclosed is a method of lightening skin or evening skin tone comprising applying the compositions of the present invention to the skin. The method can further comprise identify a person in need of lightening skin or evening skin tone. The methods can further include inhibiting melanogenesis in a skin cell, inhibiting tyrosinase or tyrosinase synthesis in a skin cell, or inhibiting melanin transport to keratinocytes in a skin cell. The composition can act as an alpha melanin stimulatory hormone antagonist. The composition can even out pigmentation of the skin. In non-limiting aspect, lightening skin can include reducing the appearance of an age spot, a skin discoloration, a freckle, a sun spot, hyper-pigmented skin, etc., by topical application of the composition to the age spot, a skin discoloration, a freckle, a sun spot, hyper-pigmented skin, etc.

Also disclosed is a method of treating hyperpigmentation comprising applying the compositions of the present invention to the skin. The method can also comprise identifying a person in need of treating hyperpigmentation and applying the composition to a portion of the skin exhibiting hyperpigmentation. Additional methods contemplated by the inventors include methods for reducing the appearance of an age spot, a skin discoloration, or a freckle, reducing or preventing the appearance of fine lines or wrinkles in skin, or increasing the firmness of skin by applying the compositions of the present invention to skin in need of such treatment.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, an anti-aging product, a deodorant, an antiperspirant, a perfume, a cologne, etc.

It is also contemplated that compositions of the present invention can be included into food-based products (e.g., beverages, fortified water, energy drinks, nutritional drinks, solid foods, vitamins, supplements, etc.) and pharmaceutical products (e.g., pills, injectable solutions, drugs, etc.). "Supplements" can include vitamins, minerals, herbs or other botanicals, amino acids, enzymes and metabolites. Such supplements are suitable for oral consumption and can be administered orally.

It is contemplated that any embodiment discussed in this specification can be implemented with respect to any method or composition of the invention, and vice versa. Furthermore, compositions of the invention can be used to achieve methods of the invention.

In one embodiment, the topical skin compositions of the current invention are pharmaceutically elegant. "Dermatologically" or "pharmaceutically elegant" describes a composition that has particular tactile properties which feel pleasant on the skin (e.g., compositions that are not too watery or greasy, compositions that have a silky texture, compositions that are non-tacky or sticky, etc.). Dermatologically or pharmaceutically elegant can also relate to the creaminess or lubricity properties of the composition or to the moisture retaining properties of the composition.

"Keratinous tissue" includes keratin-containing layers disposed as the outermost protective covering of mammals and includes, but is not limited to, skin, hair and nails.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

The term "about" or "approximately" are defined as being dose to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

The inventors discovered that a combination of jaboticaba fruit pulp and cashew fruit pulp can inhibit COX-1 and TNF-α activity in skin cells while also increasing hyaluronic acid synthesis in said cells. As illustrated by Applicant's data in Example 1, this combination synergistically acts to inhibit TNF-α activity and increase hyaluronic acid synthesis while also providing a means to inhibit COX-1 activity. Further, particular dermatologically vehicles can be used to stabily and efficiently distribute the extracts to skin while also providing the user with a pleasant feeling composition.

TNF-α or Tumor Necrosis Growth Factor Alpha is a pleiotrophic pro-inflammatory cytokine secreted by various cells including adipocytes, activated monocytes, macrophages, B cells, T cells, fibroblasts, and primary human keratinocytes. It belongs to the TNF family of ligands and signals through two receptors, TNFR1 and TNFR2. TNF-α plays a role in the induction of an inflammatory response in skin that can be caused by internal or external factors (e.g., skin irritation caused by cosmetic compositions, rash, allergic reaction, sun burn, UV radiation, cuts, scrapes, lacerations, cleansers, psoriasis, wind burns, etc.). Inhibiting TNF-α production in skin can prevent or reduce a skin inflammatory response, which in turn can help reduce the symptoms associated with erythemic skin, skin lesions, sensitive skin, inflamed skin, stress, etc.

COX-1 or Cyclooxygenase-1 is an enzyme that can help form biological mediators in cells (including skin cells) called prostanoids prostaglandins, prostacyclin, and thromboxane). Inhibition of COX-1 can reduce inflammation (such as in skin), which can help reduce the symptoms associated with erythemic skin, skin lesions, sensitive skin, inflamed skin, stress, etc.

Hyaluronic acid or hyaluronan is a component of connective tissue. It can function to cushion and lubricate joints, eyes, skin, and heart valves. Hyaluronan is also a major component of skin, where it is oftentimes involved in tissue repair. In addition to skin repair, this molecule can also act as a skin moisturizer and hydrator, can smooth out fine lines and wrinkles, and can provide elasticity to skin. With ageing, the amount of hyaluronan produced in the skin decreases, which results in loss of skin moisture and hydration, loss of skin elasticity, loss of collagen production, and increased appearance or formation of fine lines and wrinkles. By increasing production of hyaluronan in skin, the skin can maintain a youthful, soft, and smooth appearance, or can transform aged skin to have a more youthful, soft, and smooth appearance. Either way, hyaluronan can act as a prophylactic agent against the appearance of skin aging or as a treatment to hydrate skin, moisturize skin, increase the skin's elasticity, and/or reduce the appearance of fine lines or wrinkles.

These and other non-limiting aspects of the present invention are described in further detail below.

A. Plants

Jaboticaba, also known as *Myrciaria cauliflora* or the Brazilian Grape Tree, is a fruit-bearing tree native to Argentina, Brazil and Paraguay. The fruit has a purplish black skin, with a white pulp. It can be eaten raw or be used to make jellies and plain juice or wine. The inventors discovered that the pulp portion of Jaboticaba has the ability to inhibit both COX-1 and TNF-α in skin cells, while also increasing the synthesis of hyaluronic acid in such cells.

The cashew, also known as *Anacardium occidentale*, is a tree in the flowering plant family Anacardiaceae. The plant is native to northeastern Brazil. It is now widely grown in tropical climates for its cashew nut. In addition to the nut, the cashew also produces a pear-shaped fruit that develops from the receptacle of the cashew flower. This fruit is oftentimes referred to as the "cashew fruit" or "cashew apple," which ripens into a yellow and/or red structure about 5-11 cm in length. The pulp of the cashew fruit is relatively juicy. The inventors discovered that the cashew fruit pulp has the ability to inhibit TNF-α in skin cells, while also increasing the synthesis of hyaluronic acid in such cells.

Both jaboticaba fruit and cashew fruit are commercially available from LabCat, the International division of Laboratorio Catarinense (Brazil). Further, a person of ordinary skill in the art would be able to obtain jaboticaba and cashew fruit pulp by mechanical separating the pulp from the other parts of the plants, respectively.

In one non-limiting example, the pulp can be placed directly into a composition of the present invention. Alternatively it can be further processed such as by forming a puree that is then processed to be substantially free of impurities or undesired solids. The puree can then be poured into a shallow vessel and quickly exposed to low temperature, i.e., flash frozen, for example at −20° C. or lower, preferably under a vacuum for removal of water content (lyophilization). The resultant pulp can then be used in the compositions of the present invention.

In other aspects, the jaboticaba and cashew fruit pulps can be subjected to aqueous, alcoholic, aqueous/alcoholic, or oil based extraction techniques, or combinations thereof. Such extracts can then be used in the compositions of the present invention. Extraction techniques such as those mentioned are well-known to persons having ordinary skill in the art. For instance, such processes include maceration, infusion, percolation, digestion, decoction, hot continuous extraction, aqueous-alcoholic extract, counter current extract, microwave assisted extraction, ultrasound extraction, supercritical fluid extracts, phytonic extract (e.g., with hydro-flouro-carbon solvents), etc.

B. Dermatologically Acceptable Vehicles

As noted in the summary of the invention section, some of the unique aspects of the disclosed dermatologically acceptable carriers is that they have excellent tactile properties/are cosmetically elegant, are safe to use on skin, and provide an environment which allows for the jaboticaba and/or cashew fruit extracts to remain stable and effective. The carriers also allow for efficient distribution of said extracts to skin once the composition is topically applied to said skin. This efficient distribution allows for the use of minimal amounts of the jaboticaba and cashew pulp extracts to bring about the desired skin-related benefits. In one embodiment, the carrier includes 25% to 35% by weight of water, at least 35% by weight of a silicone phase comprising cyclopentasiloxane, polysilicone-11, PEG-10 dimethicone, dimethicone, 3% to 7% by weight of silica, 3% to 5% by weight of glycerin, 1 to 3% by weight of pentylene glycol, and 1% to 3% by weight of caprylic/capric triglyceride. In another aspect, the dermatologically acceptable carrier/vehicle can include 60% to 70% by weight of water, 5% to 10% by weight of alcohol, 5% to 10% by weight of dipropylene glycol, 1% to 5% by weight of methyl gluceth-20, 1% to 5% by weight of biosaccharide gum, 1% to 5% by weight of glyceryin and 1% to 5% by weight of dimethicone/vinyl dimethicone crosspolymer.

C. Compositions of the Present Invention

1. Combination and Amounts of Ingredients

It is contemplated that the compositions of the present invention can include jaboticaba fruit pulp, cashew fruit pulp, or a combination thereof or extracts thereof. The compositions can also include additional ingredients described throughout this specification. The concentrations of these pulps and/or additional ingredients can vary, in non-limiting embodiments, for example, the compositions can include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of the plant extracts identified in this specification or any combination thereof or additional ingredients. In non-limiting aspects, the percentage of such ingredients can be calculated by weight or volume of the total weight of the compositions. The concentrations can vary depending on the desired effect of the compositions or on the product into which the compositions are incorporated.

2. Composition Vehicles

The compositions of the present invention can be formulated into all types of vehicles. Non-limiting examples of suitable vehicles include emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (both aqueous and hydro-alcoholic), anhydrous bases (such as lipsticks and powders), gels, ointments, pastes, milks, liquids, aerosols, solid forms, or eye jellies. Variations and other appropriate vehicles will be apparent to the skilled artisan and are appropriate for use in the present invention. In certain aspects, the concentrations and combinations of the ingredients can be selected in such a way that the combinations are chemically compatible and do not form complexes which precipitate from the finished product.

It is also contemplated that the extracts and additional ingredients identified throughout this specification can be encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver such ingredients to skin (see, e.g., U.S. Pat. No. 6,387,398; U.S. Pat. No. 6,203,802; U.S. Pat. No. 5,411,744; Kreuter 1988).

Also contemplated are pharmaceutically-acceptable or pharmacologically-acceptable compositions. The phrase "pharmaceutically-acceptable" or "pharmacologically-acceptable" includes compositions that do not produce an allergic or similar untoward reaction when administered to a human. Typically, such compositions are prepared either as topical compositions, liquid solutions or suspensions, solid forms suitable for solution in, or suspension in, liquid prior to use can also be prepared. Routes of administration can vary with the location and nature of the condition to be treated, and include, e.g., topical, inhalation, intradermal, transdermal, parenteral, intravenous, intramuscular, intranasal, subcutaneous, percutaneous, intratracheal, intraperitoneal, intratumoral, perfusion, lavage, direct injection (e.g., an injectable solution), and oral administration and formulation (e.g., tablets, capsules, etc.).

3. Products

The compositions of the present invention can be incorporated into products. Non-limiting examples of products include cosmetic products, food-based products (e.g., fortified water, energy drinks, nutritional drinks, vitamins, supplements, solid foods), pharmaceutical products, etc. By way of example only, non-limiting cosmetic products include sunscreen products, sunless skin tanning products, hair products (e.g., shampoos, conditioners, colorants, dyes, bleaches, straighteners, and permanent wave products), fingernail products, moisturizing creams, skin creams and lotions, softeners, day lotions, gels, ointments, foundations, night creams, lipsticks and lip balms, cleansers, toners, masks, deodorants, antiperspirants, exfoliating compositions, shaving-related products (e.g., creams, "bracers" and aftershaves), pre-moistened wipes and washcloths, tanning lotions, bath products such as oils, foot care products such as powders and sprays, skin colorant and make-up products such as foundations, blushes, rouges eye shadows and lines, lip colors and mascaras, baby products (e.g., baby lotions, oils, shampoos, powders and wet wipes), and skin or facial peel products. Additionally, the cosmetic products can be formulated as leave-on or rinse-off products.

4. Additional Ingredients

Compositions of the present invention can include additional ingredients. Non-limiting examples of additional ingredients include cosmetic ingredients (both active and non-active) and pharmaceutical ingredients (both active and non-active).

a. Cosmetic Ingredients

The CTFA International Cosmetic ingredient Dictionary and Handbook (2008), 12$^{th}$ Edition, describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., *aloe vera*, chamomile, cucumber extract, *ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) waterproofing agents (e.g., magnesium/aluminum hydroxide stearate), skin conditioning agents (e.g., *aloe* extracts, allantoin, bisabolol, ceramides, dimethicone, hyaluronic acid, and dipotassium glycyrrhizate), thickening agents (e.g., substances which that can increase the viscosity of a composition such as carboxylic acid polymers, crosslinked polyacrylate polymers, polyacrylamide polymers, polysaccharides, and gums), and silicone containing compounds (e.g., silicone oils and polyorganosiloxanes). The following provides specific non-limiting examples of some of the additional ingredients that can be used with the compositions of the present invention.

i. Sunscreen Agents

UV absorption agents that can be used in combination with the compositions of the present invention include chemical and physical sunblocks. Non-limiting examples of chemical sunblocks that can be used include para-aminobenzoic acid (PABA), PARA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide). Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, 70, 80, 90 or more, or any integer or derivative therein.

ii. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated acetylated lanolin alcohol, acrylates/C10-30 alkyl acrylate crosspolymer, acrylates copolymer, alanine, algae extract, *aloe barbadensis, aloe-barbadensis* extract, *aloe barbadensis* gel, *althea officinalis* extract, aluminum starch octenylsuccinate, aluminum stearate, apricot (*prunus armeniaca*) kernel oil, arginine, arginine aspartate, *arnica montana* extract, ascorbic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (*borago officinalis*) extract, 2-bromo-2-nitropropane-1,3-diol, butcherbroom (*ruscus aculeatus*) extract, butylene glycol, *calendula officinalis* extract, *calendula officinatis* oil, candelilla (*euphorbia cerifera*) wax, canola oil, caprylic/capric triglyceride, cardamon (*elettaria cardamomum*) oil, carnauba (*copernicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, *eucalyptus globulus* oil, evening primrose (*oenothera biennis*) oil, fatty acids, tructose, gelatin, *geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated coca-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, *macadamia ternifolia* nut oil, magnesium stearate, magnesium sulfate, maltitol, matricaria (*chamomilla recutita*) oil, methyl glucose sesquistearate, methylsilanol PCA, microcrystalline wax, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate octyl palmitate, octyl salicylate, octyl, stearate, oleic acid, olive (*olea europaea*) oil, orange (*citrus aurantiurn dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate. PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipaimitate, quatemium-15, quatemiura-18 hectorite, quaternium-22, retinol, retinyl palmitate, rice (*oryza saliva*) bran oil, RNA, rosemary (*rosmarinus officinalis*) oil, rose oil, safflower (*carthamus tinctorius*) oil, sage (*salvia officinalis*) oil, salicylic acid, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethyisilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

iii. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

iv. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, paltnitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

v. Emulsifiers

In some non-limiting aspects, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate, 60, glyceryl stearate, PEG-100 stearate, and mixtures thereof.

vi. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si——O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In preferred aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethyisiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

vii. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, *geranium* oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose ono oil, rosemary oil, sandalwood oil, spearmint oil, spikenard oil, vetiver oil, wintergreen oil, or ylang, ylang. Other essential oils known to those of skill in the art are also contemplated as being useful within the context of the present invention.

viii. Thickening Agents

Thickening agents, including thickener or gelling agents, include substances that can increase the viscosity of a composition. Thickeners include those that can increase the viscosity of a composition without substantially modifying the efficacy of the active ingredient within the composition. Thickeners can also increase the stability of the compositions of the present invention.

Non-limiting, examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with ally ethers of sucrose or pentaervtritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

b. Pharmaceutical Ingredients

Pharmaceutical ingredients are also contemplated as being useful with the emulsion compositions of the present invention. Non-limiting examples of pharmaceutical ingredients include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

D. Kits

Kits are also contemplated as being used in certain aspects of the present invention. For instance, a composition of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of a composition. In other embodiments, the container can be squeezed (e.g., metal, laminate, or plastic tube) to dispense a desired amount of the composition. The composition can be dispensed as a spray, foam, an aerosol, a liquid, a fluid, or a semi-solid. The containers can have spray, pump, or squeeze mechanisms. A kit can also include instructions for using the kit and/or compositions. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Materials and Methods for Obtaining Fruit Pulp

Jaboticaba fruit pulp and cashew fruit pulp used for this experiment were obtained from LabCat, the International division of Laboratorio Catarinense (Brazil). The fruit pulp for both extracts were prepared by obtaining the pulp and subjecting it to spray drying in the presence of maltodextrine. The dried product was subsequently homogenized with a mixer and packaged for storage in powdered form.

Example 2

Data

Table I includes a summary of the data obtained concerning the jaboticaba fruit pulp and cashew fruit pulp described in Example 1.

TABLE 1

| Extract | COX-1 Assay | TNF-α Assay | Hyaluronic Acid Synthesis Assay |
|---|---|---|---|
| Cashew fruit pulp | — | −43.31% | 89% |
| Jaboticaba fruit pulp | −23.08% | −25.83% | 118% |

The inventors discovered a synergy between these two pulps in that the combination of both provides for COX-1 and TNF-α inhibition and also increases hyaluronic acid synthesis. The benefit of inhibiting both COX-1 and TNF-α provides a dual or synergistic response in inhibiting an inflammatory response such as a skin inflammatory response.

The assays described in the following paragraphs were used to obtain the data illustrated in Table 1. These assays can also be used to test fruit pulp of jaboticaba and/or cashew or extracts thereof or to test compositions having such pulps or extracts, and the ability of such pulps or extracts or composition to inhibit COX-1, TNF-α, and/or increase hyaluronic acid synthesis.

COX-1 Assay:

An in vitro cyclooxygenase-1 (COX-1) inhibition assay was used. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes COX-1 enzymes in order to screen isozyme-specific inhibitors. The Colormetric COX (ovine) Inhibitor screening assay (#760111, Cayman Chemical), was used to analyze the effects of test extracts on the activity of purified cyclooxygnase enzyme-1 (COX-1). According to manufacturer instructions, purified enzyme, home and test extracts were mixed in assay buffer and incubated with shaking for 15 min at room temperature. Following incubation, arachidonic acid and colorimetric substrate were added to initiate the reaction. Color progression was evaluated by colorimetric plate reading at 590 nm. The percent inhibition of COX-1 activity was calculated compared to non-treated controls to determine the ability of test extracts to inhibit the activity of purified enzyme.

Tumor Necrosis Factor Alpha (TNF-α) Assay:

The anti-irritant capability of the extracts identified in Table 1 were evaluated by measuring inhibition of TNF-α release by primary human keratinocytes in response to stress. Primary human keratinocytes were induced to release TNF-α, a pleiotropic cytokine that plays a central role in inflammation, in the presence or absence of the extract. TNF-α secretion was quantified using R&D Systems (Minneapolis, Minn. USA) TNF-α Enzyme-linked Immunosorbant Assay #DTA00C according to manufacturer instructions. This sandwich immunoassay technique used color development to quantify the amount of TNF-α present in the cellular supernatant. Color developed in proportion to the amount of TNF-α and was detected at 450 nm using a microplate reader. Data were calculated as % inhibition of the untreated controls. Negative values demonstrated the ability of test ingredients to inhibit the production of TNF-α compared to controls. Extracts that have the ability to inhibit TNF-α activity can reduce or prevent the deleterious effects caused by the inflammatory pathway (e.g., reduce skin inflammation, treat or prevent inflammatory diseases, etc.).

Hyaluronic Acid Synthesis Assay:

The capability of the extracts identified in Table 1 to stimulate synthesis of hyaluronic acid (HA) was evaluated by measuring HA release by primary human epidermal fibroblasts. HA is an abundant glycosaminoglycan found in the extracellular matrix in skin. HA plays an important role in wound healing and moisturization. Primary human epidermal fibroblasts were seeded into 96 well plates in DMEM with 10% fetal bovine serum and incubated at 37° C. and 10% CO2 for 24 hours. Upon reaching 30% confluence, cells were incubated 3 days in DMEM with 0.15% fetal bovine serum. Cells were then treated with extracts in DMEM with 10% fetal bovine serum and incubated at 37° C. and 10% CO2 for 24 hours. HA secretion was quantified using R&D Systems (Minneapolis, Minn. USA) HA Enzyme-linked Immunosorbant Assay # DY3614 according to manufacturer instructions. This sandwich immunoassay technique used color development to quantify the amount of HA present in the cellular supernatant. Color developed in proportion to the amount of HA and was detected at 450 nm using a micropiate reader. Data were calculated as % of the untreated controls. Positive values demonstrated the ability of test ingredients to stimulate the production of HA compared to controls. Extracts that have the ability to stimulate HA production can improve skin moisturization and firmness.

Example 3

Testing Vehicles

Tables 2 and 3 describe generic skin testing formulations in which a skin active ingredient can be incorporated into to determine the types of skin benefits that can be attributed to the skin active ingredient. These formulations are prepared in such a manner that any resulting skin benefit from topical application of the formula to skin can be directly attributed to the skin active ingredient being tested.

TABLE 2*

| Ingredient | % Concentration (by weight) |
|---|---|
| Phase A | |
| Water | 84.80 |
| Xanthum gum | 0.1 |
| M-paraben | 0.15 |
| P-paraben | 0.1 |
| Citric acid | 0.1 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C** | |
| Skin Active Ingredient | 2.0 |
| TOTAL | 100 |

*Procedure for making composition: Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**The fruit pulps identified throughout this specification can be incorporated into this testing formulation as the skin active ingredient. The pulps can be individually used or combined in this testing vehicle. The concentration ranges of the pulp (or combination of pulps) can be modified as desired or needed by increasing or decreasing the amount of water. For instance, jaboticaba fruit pulp or cashew fruit pulp or extracts thereof or a combination of both can be tested in the Table 2 formulation.

TABLE 3*

| Ingredient | % Concentration (by weight) |
|---|---|
| Phase A | |
| Water | 78.6 |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C** | |
| Skin Active Ingredient | 2.0 |
| TOTAL | 100 |

*Add ingredients in phase A to beaker and heat to 70-75° C. while mixing. Subsequently, add the phase B ingredient with phase A and cool to 30° C. with mixing. Subsequently, add phase C ingredient while mixing.
**The fruit pulps identified throughout this specification can be incorporated into this testing formulation as the skin active ingredient. The pulps can be individually used or combined in this testing vehicle. The concentration ranges of the pulp (or combination of pulps) can be modified as desired or needed by increasing or decreasing the amount of water. For instance, jaboticaba fruit pulp or cashew fruit pulp or extracts thereof or a combination of both can be tested in the Table 2 formulation.

Example 4

Dermatologically Acceptable Vehicles

Tables 4 and 5 describe dermatologically acceptable vehicles that provide a stable environment for the jaboticaba and cashew pulp extracts, while also providing an efficient distribution of said extracts to skin (data not shown).

As noted in the summary of the invention section, some of the unique aspects of the disclosed dermatologically acceptable carriers is that they have, excellent tactile properties/are cosmetically elegant, are safe to use on skin, and provide an environment which allows for the jaboticaba and/or cashew fruit extracts to remain stable and effective. The carriers also allow for efficient distribution of said extracts to skin once the composition is topically applied to said skin. This efficient distribution allows for the use of minimal amounts of the jaboticaba and cashew pulp extracts to bring about the desired skin-related benefits.

TABLE 4*

| Ingredient | % Concentration (by weight) |
|---|---|
| Phase A | |
| Water | 25 to 35 |
| Phase B | |
| Cyclopentasiloxane | 25 to 30 |
| Polysilicone-11 | 5 to 10 |
| Silica | 3 to 7 |
| PEG-10 Dimethicone | 2 to 5 |
| Dimethicone | 2 to 5 |
| Pentylene Glycol | 1 to 3 |
| Caprylic/Capric Triglyceride | 1 to 3 |
| Extract(s)** | 0.1 to 5 |
| TOTAL*** | 100 |

*Standard mixing, heating, and cooling procedures can be used. For instance, one can mix phase A with B in the presence of heat. Extract(s) can be added and the composition can be cooled to room temperature (20-25° C.).
**The fruit pulps can be added individually or in combination.
***Stable formulation having the desired skin efficacy benefits (see Table 1) was produced in line with the ranges provided in Table 4.

TABLE 5*

| Ingredient | % Concentration (by weight) |
|---|---|
| Phase A | |
| Water | 60 to 70 |
| Phase B | |
| Alcohol denat. | 5 to 10 |
| Dipropylene Glycol | 5 to 10 |
| Methyl Gluceth-20 | 2 to 5 |
| Biosaccharide Gum-1 | 2 to 5 |
| Glycerin | 1 to 3 |
| Dimethicone/Vinyl Dimethicone Crosspolymer | 1 to 3 |
| Extract(s)** | 0.1 to 5 |
| TOTAL*** | 100 |

*Standard mixing, heating, and cooling procedures can be used. For instance, one can mix phase A with B in the presence of heat. Extract(s) can be added and the composition can be cooled to room temperature (20-25° C.).
**The fruit pulps can be added individually or in combination.
***Stable formulation having the desired skin efficacy benefits (see Table 1) was produced in line with the ranges provided in Table 5.

Example 5

Additional Assays that can be Used to Test Compositions

Compositions comprising jaboticaba fruit pulp and cashew fruit pulp identified throughout the specification, or a combination of such pulps (including, for example, the pulps described in Example 1, the testing formulations identified in Tables 2-3, and the vehicles identified in Tables 4-5), can be determined by methods known to those of ordinary skill in the art. The following are non-limiting assays that can be used in the context of the present invention. It should be recognized that other testing procedures can be used, including, for example, objective and subjective procedures.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with a composition of the present invention. Repeat measurements are taken at regular intervals to determine the formula's ability to reduce redness and irritation.

Skin Moisture/Hydration Assay:

Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture, Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al. (1978):

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and of the replicas covered by wrinkles or fine lines was determined.

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique cart be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis), MELANODERM™ Assay:

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

ORAC Assay:

Oxygen Radical Absorption (or Absorbance) Capacity (ORAC) of the aromatic skin-active ingredients and compositions can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of the aromatic skin-active ingredients and compositions can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

All of the active ingredients, compositions, or methods disclosed and claimed in this specification can be made and executed without undue experimentation in light of the present disclosure. While the active ingredients, compositions, or methods of this invention have been described in terms of particular embodiments, it will be apparent to those of skill in the art that variations may be applied to the active ingredients, compositions, or methods and in the steps or in the sequence of steps of the method described herein without departing from the concept, spirit and scope of the invention.

The invention claimed is:

1. A method of treating a fine line or wrinkle or erythemic skin, the method comprising topically applying to a fine line or wrinkle or erythemic skin a composition comprising spray-dried *Myrciaria cauliflora* fruit pulp, wherein the composition increases hyaluronic acid synthesis in the skin or reduces TNF-α or COX-1 activity in the skin.

2. The method of claim 1, wherein the *Myrciaria cauliflora* fruit pulp is spray-dried in the presence of maltodextrin.

3. The method of claim 1, wherein the *Myrciaria cauliflora* fruit pulp consists of the pulp portion of *Myrciaria cauliflora*.

4. The method of claim 1, wherein the composition further comprises a dermatologically acceptable vehicle having at least 60 wt. % of water.

5. The method of claim 4, wherein the dermatologically acceptable vehicle further comprises:
    5 to 10 wt. % of alcohol;
    5 to 10 wt. % of dipropylene glycol;
    1 to 5 wt. % of methyl gluceth-20;
    1 to 5 wt. % of biosaccharide gum;
    1 to 5 wt. % of glycerin; and
    1 to 5 wt. % of dimethicone/vinyl dimethicone crosspolymer.

6. The method of claim 1, wherein the composition is an oil-in-water emulsion, and wherein the composition further comprises an emulsifier.

7. The method of claim 1, wherein the composition is a gel.

8. The method of claim 1, wherein the composition further comprises a polyorganosiloxane.

9. The method of claim 8, wherein the polyorganosiloxane is dimethicone or cyclomethicone or a combination thereof.

10. The method of claim 1, wherein the composition further comprises a preservative selected from methylparaben, propylparaben, or a combination thereof.

* * * * *